United States Patent [19]

Kasuga et al.

[11] Patent Number: 5,246,889

[45] Date of Patent: * Sep. 21, 1993

[54] GLASS-CERAMIC AND ARTIFICIAL DENTAL CROWN FORMED THEREFROM

[75] Inventors: Tomoko Kasuga, Akishima; Toshihiro Kasuga, Nagoya, both of Japan

[73] Assignee: Hoya Corporation, Tokyo, Japan

[*] Notice: The portion of the term of this patent subsequent to Nov. 19, 2008 has been disclaimed.

[21] Appl. No.: 841,190

[22] Filed: Feb. 26, 1992

[30] Foreign Application Priority Data

Mar. 7, 1991 [JP] Japan .................................. 3-67881

[51] Int. Cl.$^5$ ...................... C03C 10/04; C03C 10/16
[52] U.S. Cl. ........................................... 501/3; 501/5; 501/69; 501/70; 106/35
[58] Field of Search ........................... 501/5, 3, 69, 70; 106/35

[56] References Cited

U.S. PATENT DOCUMENTS

| | | | |
|---|---|---|---|
| 4,467,039 | 8/1984 | Beall et al. | 501/3 |
| 5,066,619 | 11/1991 | Kasuga et al. | 501/3 |

FOREIGN PATENT DOCUMENTS

| | | |
|---|---|---|
| 59-50046 | 3/1984 | Japan . |
| 59-207850 | 11/1984 | Japan . |
| 62-70244 | 3/1987 | Japan . |

*Primary Examiner*—Karl Group
*Attorney, Agent, or Firm*—Nixon & Vanderhye

[57] ABSTRACT

A glass-ceramic which is excellent in mechanical strength, cutting processability and chemical durability and suitable for the production of an artificial dental crown and a mold, the glass-ceramic containing, by weight percentage, 2 to 17% of CaO, 0 to 5% of $K_2O$, 0 to 4% of $Na_2O$, the total content of $K_2O$ and $Na_2O$ being 0.5–7%, 15 to 35% of MgO, 30 to 49% of $SiO_2$, 2 to 15% of $ZrO_2$ and not more than 14% (calculated as F) of fluorine, and having a zirconia crystal and a mica crystal precipitated.

6 Claims, 1 Drawing Sheet

GLASS-CERAMIC AND ARTIFICIAL DENTAL CROWN FORMED THEREFROM

FIELD OF THE INVENTION

The present invention relates to a glass-ceramic which is excellent in mechanical strength, machinability (cutting processability) and chemical durability. The glass-ceramic of the present invention is particularly useful as a material for an artificial dental crown and a material for a mold used for the production of plastic articles and ophthalmic lenses.

PRIOR ART OF THE INVENTION

In recent years, a machinable ceramic produced by precipitation of a mica crystal is used as a material for the production of a dental crown more beautiful and more excellent in biocompatibility than a metal material.

For example, JP-A-59-50046 ("prior art 1" hereinafter) discloses a ceramic produced by precipitation of fluorotetrasilicon mica ($KMg_{2.5}Si_4O_{10}F_2$) from a glass containing $SiO_2$, $MgO$, $MgF_2$, $K_2O$, $ZrO_2$, $Al_2O_3$, etc., as main components. This ceramic is improved in contamination resistance by means of a small amount of $Al_2O_3$ or $ZrO_2$.

JP-A-62-70244 ("prior art 2" hereinafter) discloses a ceramic having improved mechanical strength, which is obtained by precipitation of mica ($Na.Mg_3.(Si_3AlO_{10})F_2$), β-eucryptite ($Li_2O.Al_2O_3.2SiO_2$) and β-spodumene ($Li_2O.Al_2O_3.4SiO_2$) from a glass containing $SiO_2$, $MgO$, $Na_2O$, $Li_2O$, $ZrO_2$, $TiO_2$, $Al_2O_3$, fluorine, etc., as main components.

Further, JP-A-59-207850 ("prior art 3" hereinafter) discloses a crystallized glass produced by precipitation of potassium fluororichterite from a glass containing, by weight percentage, 50 to 70% of $SiO_2$, 4 to 15% of $CaO$, 8 to 25% of $MgO$, 2 to 9% of $Na_2O$ and 2 to 12% of $K_2O$. This prior art 3 describes that a mica crystal in a metastable phase is formed at a temperature in the range of 600° to 800° C. at a stage before the precipitation of potassium fluororichterite and further that potassium fluororichterite is formed by heating the above mica crystal in a metastable phase at a temperature of 800° C. or higher.

However, the bending strength of the machinable ceramic described in the above prior art 1 (JP-A-59-50046) is about 1,500 kg/cm² (147 MPa). The bending strength of the machinable ceramic described in the above prior art 2 (JP-A-62-70244) is about 2,200 kg/cm² (215.6 MPa). When these machinable ceramics are used as a dental crown, it is required to cut the dentin or tooth at least 1 mm deep to secure strength, and they are applied only to limited places. Further, since these ceramics are insufficient in bending strength, it is required to fully take care when a dental crown is produced therefrom or when the dental crown is fitted.

Further, the glass-ceramic disclosed in the above prior art 3 (JP-A-52-207850) has a defect in that since the above mica is precipitated only in a metastable phase, it is difficult to precipitate a mica crystal stably from the glass of this prior art 3. The reason therefor is as follows; Since the $SiO_2$ content in the glass of the prior art 3 is as large as 50 to 70% by weight, the glass is stabilized, and it is eventually difficult to precipitate a large amount of a fine mica crystal.

When a glass-ceramic is used as a dental crown, it is placed in an oral cavity under severe conditions for a long time. Therefore, a material which is excellent not only in mechanical strength but also in chemical durability is being desired. Further, a material having light transmission property is being desired from an aesthetical point of view.

SUMMARY OF THE INVENTION

It is therefore an object of the present invention to provide a glass-ceramic which is excellent in mechanical strength, machinability (cutting processability) and chemical durability and is suitable as a material for the production of a dental crown and a mold.

The above object of the present invention is achieved by a glass-ceramic containing, by weight percentage,

| | |
|---|---|
| CaO | 2–17%, |
| $K_2O$ | 0–5% |
| $Na_2O$ | 0–4% | the total content of $K_2O$ and $Na_2O$ being 0.5–7%,

| | |
|---|---|
| MgO | 15–35% |
| $SiO_2$ | 30–40% |
| $Al_2O_3$ | 5–30% |
| $ZrO_2$ | 2–15%, and |
| fluorine (calculated as F) | not more than 14%, | and having at least a zirconia crystal and a mica crystal precipitated.

DETAILED DESCRIPTION OF THE INVENTION

Figure 1:
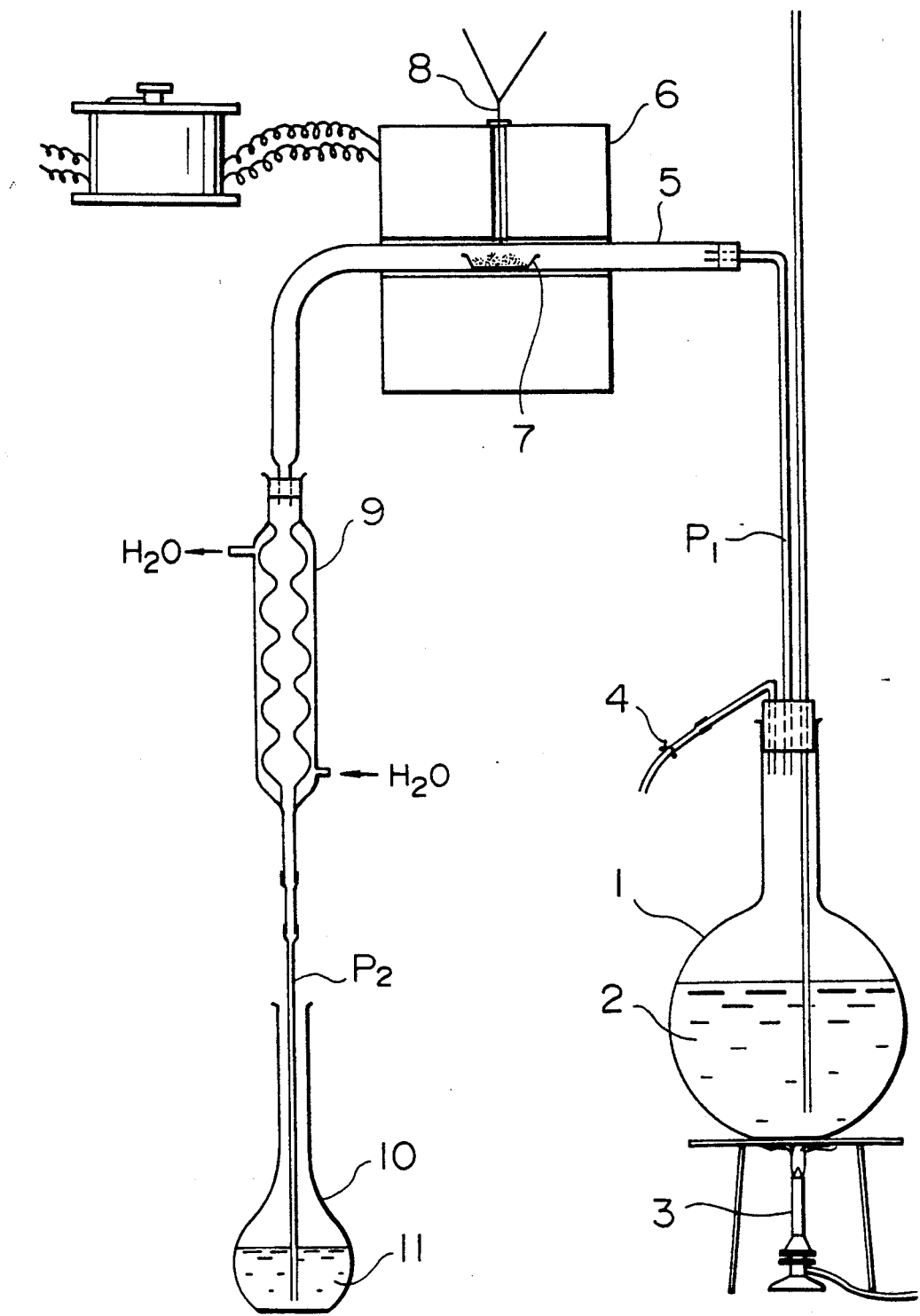
FIG. 1 shows a schematic view of an apparatus for measuring the fluorine content in a glass-ceramic of the present invention.

In the glass-ceramic of the present invention, the components and their contents are limited for the following reasons.

CaO has an effect of precipitating a mica crystal to improve the machinability (cutting processability) and an effect of lowering the viscosity of glass. When the CaO content is less than 2% by weight, the amount of a precipitated mica crystal decreases, and the resultant glass-ceramic is poor in machinability (cutting processability). When the CaO content exceeds 17% by weight, the glass tends to cause devitrification. The CaO content is therefore limited to 2 to 17% by weight, preferably to 5 to 15% by weight.

$K_2O$ and $Na_2O$ have an effect of forming a fine mica crystal during the precipitation by heat treatment and improving the chemical durability. The chemical durability depends upon the amount of a residual glass in the glass-ceramic. With a decrease in the amount of the residual glass, the chemical durability is more improved. $K_2O$ and $Na_2O$ improve the chemical durability, and it is therefore required to incorporate at least one of these. When, however, the $K_2O$ content exceeds 5% by weight, the devitrification tends to occur. Therefore, the $K_2O$ content is limited to 0 to 5% by weight, preferably 1 to 3.5% by weight. Further, when the $Na_2O$ content exceeds 4% by weight, a mica crystal containing a large amount of sodium precipitates, and the resultant glass-ceramic undesirably shows a decrease in mechanical strength. The $Na_2O$ content is therefore limited to 0 to 4% by weight, preferably 0.5 to 1.8%. When the total content of $K_2O$ and $Na_2O$ is less than 0.5% by weight, the mica precipitated by heat treatment shows increased swelling properties. When the total content of $K_2O$ and $Na_2O$ exceeds 7% by weight, the glass tends to cause devitrification. The total content of $K_2O$ and $Na_2O$ is therefore limited to 0.5 to 7% by weight, preferably 1.5 to 5.3% by weight.

MgO is one of main components in a mica crystal. When the MgO content is less than 15% by weight, the glass is stabilized, and it is difficult to precipitate a crystal. When the MgO content exceeds 35% by weight, the amount of precipitated mica crystal decreases. The MgO content is therefore limited to 15 to 35% by weight, preferably 19 to 30% by weight.

$SiO_2$ is a major component which forms a skeleton of glass. When the $SiO_2$ is less than 30% by weight, the glass tends to cause devitrification. When the $SiO_2$ content exceeds 49% by weight, the viscosity increases, and it is difficult to obtain a homogeneous glass. The $SiO_2$ content is therefore limited to 30 to 49% by weight, preferably 40 to 49% by weight.

$Al_2O_3$ is one of main components in a mica crystal, and has an effect of precipitating a stabler mica crystal and improving chemical durability. When the $Al_2O_3$ content is less than 5% by weight, the glass tends to cause devitrification. When the $Al_2O_3$ content exceeds 30% by weight, the viscosity increases, and it is difficult to obtain a homogeneous glass. The $Al_2O_3$ content is therefore limited to 5 to 30% by weight, preferably 7 to 17% by weight.

$ZrO_2$ is a component which forms a zirconia crystal and improves the glass in mechanical strength. Even when the $ZrO_2$ content is less than 2% by weight, it produces an effect as a nucleating agent, and a homogeneous and fine mica crystal can be precipitated. However, a zirconia crystal which contributes to an improvement of the glass-ceramic in strength does not precipitate. When the $ZrO_2$ content exceeds 15% by weight, it is difficult to obtain a homogeneous glass. The $ZrO_2$ content is therefore limited to 2 to 15% by weight, preferably 3 to 12% by weight.

Fluorine is a component to precipitate a mica crystal. When the fluorine content (calculated as fluorine) exceeds 14% by weight, the glass tends to cause devitrification. Therefore, the fluorine content is limited to not more than 14% by weight. When the fluorine content is less than 1.5% by weight, it is difficult to precipitate a mica crystal, and it is difficult to obtain a glass-ceramic imparted with cutting processability. Therefore, the preferable fluorine content is not less than 1.5% by weight. The fluorine content is particularly preferably 7 to 14%.

In addition to the above eight essential components, the glass-ceramic of the present invention may contain at least one oxide selected from SrO, $TiO_2$, $Nb_2O_5$, $Ta_2O_5$ and $Y_2O_3$, and the amount of such oxide(s) is 5% by weight or below. When the content of these optional components exceeds 5% by weight, the glass tends to cause devitrification, it is difficult to obtain a homogeneous glass, and the content of formed mica decreases. The total content of the essential components of CaO, $K_2O$, $Na_2O$, MgO, $SiO_2$, $Al_2O_3$, $ZrO_2$ and fluorine is preferably at least 95% by weight.

The glass-ceramic of the present invention has at least a zirconia crystal and a mica crystal as a precipitated crystal. In the glass-ceramic of the present invention, the zirconia crystal mainly contributes to an improvement in mechanical strength, and the mica crystal mainly contributes to an improvement in machinability (cutting processability).

In the production of the glass-ceramic of the present invention, there are some cases where there occurs the precipitation of some of an enstatite ($MgO.SiO_2$) crystal, an akermanite ($2CaO.MgO.2SiO_2$) crystal, a diopside ($CaO.MgO.2SiO_2$) crystal, an anorthite ($CaO.Al_2O_3.2SiO_2$) crystal, a richterite ($Na.NaCa.Mg_5.Si_8O_{22}F_2$) crystal and a forsterite ($2MgO.SiO_2$) crystal. The precipitation of these crystals is rather preferred for an improvement in strength. Therefore, the glass-ceramic of the present invention may contain at least one of the above crystals.

The glass-ceramic of the present invention is produced by mixing various raw materials to form a glass-ceramic containing, by weight percentage,

| CaO | 2–17%, |
|---|---|
| $K_2O$ | 0–5% |
| $Na_2O$ | 0–4% | the total content of $K_2O$ and $Na_2O$ being 0.5–7%,

| MgO | 15–35% |
|---|---|
| $SiO_2$ | 30–49% |
| $Al_2O_3$ | 5–30% |
| $ZrO_2$ | 2–15%, and |
| fluorine (calculated as F) | not more than 14%, | melting the resultant mixture, cooling the melt to room temperature to obtain a glass and heat-treating the glass at a temperature in the range in which a zirconia crystal and a mica crystal are precipitated. The heat treatment for the precipitation of the intended crystals is carried out either by a one-step method in which the above glass is heat-treated at a temperature in the range where the intended crystals are precipitated or by a two-step method in which the above glass is heat-treated at a temperature which is higher than the glass transition temperature by 10° to 200° C. and then heat-treated at a temperature which is higher than the glass transition temperature by 200° to 500° C.

The temperature range for the formation of the above crystals can be determined by differential thermal analysis of the glass. The X-ray diffraction data of the glass heat-treated at an exothermic peak temperature in the DTA curve is analyzed to measure the precipitation temperature corresponding to the exothermic peak, and the range from the initiation of the heat generation to the termination of the heat generation is taken as the temperature range for the crystal precipitation. Concerning the precipitated crystals, the mica crystal improves the machinability (cutting processability), and the zirconia crystal improves the mechanical properties. The temperature for the crystal precipitation is preferably in the range of 750° to 1,200° C.

According to a detailed study of the present inventors, it has been shown that the zirconia crystal precipitation temperature and the mica crystal precipitation temperature are very close to each other. Therefore, the heat-treatment may be carried out at one step at a temperature in the precipitation temperature range of the intended crystals. However, it is difficult to control the precipitation of the crystals. It is therefore advantageous to carry out the heat treatment at two steps, in which nuclei of precipitated crystals are fully formed at a temperature higher than the glass transition temperature by 10° to 200° C., and then the glass is heat-treated at a temperature higher than the glass transition temperature by 200° to 500° C., whereby a large amount of the zirconia crystal and a large amount of the mica crystal can be precipitated.

The reasons for a strength improvement in the glass-ceramic due to the precipitation of the zirconia crystal are considered as follows. When tetragonal zirconia precipitates, the glass-ceramic is improved in strength presumably due to its stress-induced transformation. When the precipitated zirconia crystal is monoclinic or cubic, the stress-induced transformation does not occur. However, the glass-ceramic is improved in strength presumably due to a compressive stress on the mica crystal by the precipitation of zirconia. The zirconia crystal sometimes precipitates in the grain boundary of the mica crystal and sometimes precipitates within the mica crystal depending upon the composition and amount thereof. In the former case, the strength is improved due to stress-induced transformation, and in the latter case, the strength is improved due to a residual compressive stress. Therefore, the crystal system of the precipitated zirconia crystal is not specially limited.

The thus-obtained glass-ceramic is not only excellent in mechanical strength and machinability (cutting processability) but also excellent in chemical durability. Therefore, a dental crown can be produced from this glass-ceramic. That is, a block (e.g., size of 20×20×50 mm) of this glass-ceramic is machined by means of a lathe or a drill using diamond, carborundum, SiC or stainless steel, whereby a dental crown formed from the glass-ceramic can be obtained. A dental crown can be also produced by a CAD/CAM system using a computer.

Further, a dental crown of the above glass-ceramic can be also produced by mixing various raw materials so as to form the above-described glass-ceramic composition, melting the mixture under heat to form a glass melt, casting the glass melt into a crown-shaped mold, annealing the cast article or cooling it to room temperature to form a glass having the form of a dental crown, and subjecting the glass to the heat treatment. Further, a mold used for the production of plastic articles and ophthalmic lenses can be produced from the glass-ceramic of the present invention.

The present invention will be described further in detail by reference to Examples. However, the present invention shall not be limited to the Examples.

EXAMPLES 1-21

Glass Ceramics

Oxides, carbonates, fluorides, etc., such as $CaCO_3$, $K_2CO_3$, $Na_2CO_3$, $MgO$, $MgF_2$, $Al_2O_3$, $SiO_2$ and $ZrO_2$ were used as raw materials. These raw materials were mixed in such proportions that glass-ceramics having compositions shown in Tables 1 to 6 were obtained. The resultant mixtures were respectively charged into a platinum crucible and melted at 1,400° to 1,550° C. for 60 to 120 minutes. Then, each melted glass was cast, and annealed to room temperature to prepare a bulk glass. These bulk glasses had a glass transition point between 550° C. and 650° C. The bulk glasses were placed in an electric furnace, heated from room temperature to a predetermined temperature within the range of 800° to 1,200° C. at a constant temperature heating rate of 3° C./minute, and crystallized at the predetermined temperature for 0.5 to 10 hours. Then, the resultant products were respectively cooled to room temperature in the furnace to give glass-ceramics of Examples 1 to 21.

Part of each of the above-obtained glass-ceramics was pulverized, and precipitated crystals were identified by X-ray diffraction. These glass-ceramics were also evaluated on mechanical strength, i.e., measured for a bending strength by a three-point bending strength test method (JIS R 1601). Further, these ceramics were evaluated on their machinability by drilling a hole in them with a 1.5 mm$\phi$ drill made of tool steel to see whether or not the hole could be drilled. Tables 1 to 6 show the results, in which ceramics that were machinable are shown as C, ceramics that were well machinable are shown as B, and ceramics that were excellently machinable are shown as A.

TABLE 1

|  | Example | | | |
|---|---|---|---|---|
|  | 1 | 2 | 3 | 4 |
| COMPOSITION (wt %) | | | | |
| CaO | 7.5 | 16.5 | 3.4 | 2.2 |
| $K_2O$ | 0.3 | 4.8 | 1.4 | 0.7 |
| $Na_2O$ | 0.5 | 0.2 | 0.2 | 2.2 |
| MgO | 34.7 | 20.5 | 17.2 | 19.2 |
| $SiO_2$ | 30.7 | 43.0 | 49.0 | 41.0 |
| $Al_2O_3$ | 12.3 | 5.3 | 22.9 | 21.6 |
| $ZrO_2$ | 6.0 | 4.0 | 2.5 | 5.6 |
| F | 8.0 | 5.7 | 3.4 | 7.5 |
| Temperature for heat treatment (°C.) | 850 | 1,050 | 950 | 950 |
| Time for heat treatment (h) | 10 | 10 | 2 | 2 |
| Precipitated crystals | mica zirconia enstatite | mica zirconia enstatite diopside | mica zirconia anorthite | mica zirconia anorthite |
| Bending strength (MPa) | 250 | 350 | 320 | 300 |
| Machinability | A | B | A | A |

Machinability:
A : excellently machinable
B : well machinable
C : machinable

TABLE 2

|  | Example | | | |
|---|---|---|---|---|
|  | 5 | 6 | 7 | 8 |
| COMPOSITION (wt %) | | | | |
| CaO | 5.4 | 5.8 | 6.5 | 8.9 |
| $K_2O$ | 2.2 | 2.4 | 0.5 | 3.7 |
| $Na_2O$ | 0.8 | 1.9 | 0.9 | 3.9 |
| MgO | 21.9 | 23.7 | 26.0 | 16.0 |
| $SiO_2$ | 40.3 | 43.6 | 44.3 | 45.1 |
| $Al_2O_3$ | 11.7 | 12.7 | 10.8 | 8.7 |
| $ZrO_2$ | 10.6 | 2.4 | 2.2 | 7.3 |
| F | 7.1 | 7.5 | 8.8 | 6.4 |
| Temperature for heat treatment (°C.) | 950 | 1,100 | 950 | 900 |
| Time for heat treatment (h) | 2 | 0.5 | 1 | 3 |
| Precipitated crystals | mica zirconia anorthite enstatite | mica zirconia richterite forsterite enstatite | mica zirconia dipside richterite esteatite | mica zirconia richterite dipside |
| Bending strength (MPa) | 400 | 290 | 270 | 300 |
| Machinability | B | B | A | B |

Machinability:
A : excellently machinable
B : well machinable
C : machinable

TABLE 3

| | Example | | | |
|---|---|---|---|---|
| | 9 | 10 | 11 | 12 |
| COMPOSITION (wt %) | | | | |
| CaO | 8.1 | 9.2 | 4.8 | 2.4 |
| $K_2O$ | 0.8 | 2.3 | 2.0 | 0.7 |
| $Na_2O$ | 3.7 | 0.4 | — | 0.8 |
| MgO | 20.4 | 24.4 | 26.2 | 20.6 |
| $SiO_2$ | 33.5 | 28.3 | 39.1 | 39.9 |
| $Al_2O_3$ | 29.1 | 13.0 | 11.0 | 14.4 |
| $ZrO_2$ | 2.8 | 13.0 | 8.7 | 7.7 |
| F | 1.6 | 9.4 | 8.2 | 13.5 |
| Temperature for heat treatment (°C) | 1,200 | 950 | 1,000 | 1,000 |
| Time for heat treatment (h) | 0.5 | 2 | 1 | 1 |
| Precipitated crystals | mica zirconia richtertie forsterite | mica zirconia diopside | mica zirconia dipside | mica zirconia enstatite |
| Bending strength (MPa) | 270 | 270 | 550 | 320 |
| Machinability | C | B | B | B |

Machinability:
A : excellently machinable
B : well machinable
C : machinable

TABLE 4

| | Example | | | |
|---|---|---|---|---|
| | 13 | 14 | 15 | 16 |
| COMPOSITION (wt %) | | | | |
| CaO | 3.2 | 5.7 | 6.1 | 5.2 |
| $K_2O$ | 0.5 | 2.2 | 1.7 | 2.0 |
| $Na_2O$ | 0.2 | 0.8 | 1.0 | 0.9 |
| MgO | 25.0 | 21.8 | 22.6 | 20.8 |
| $SiO_2$ | 39.2 | 40.0 | 48.7 | 45.2 |
| $Al_2O_3$ | 17.4 | 11.6 | 6.5 | 13.0 |
| $ZrO_2$ | 2.5 | 10.5 | 3.5 | 4.0 |
| F | 12.0 | 7.4 | 9.9 | 8.9 |
| Temperature for heat treatment (°C) | 800 | 1,000 | 950 | 950 |
| Time for heat treatment (h) | 10 | 3 | 2 | 2 |
| Precipitated crystals | mica zirconia enstatite | mica zirconia | mica zirconia akermanite richterite | mica zirconia enstatite |
| Bending strength (MPa) | 290 | 430 | 310 | 320 |
| Machinability | B | B | A | A |

Machinability:
A : excellently machinable
B : well machinable
C : machinable

TABLE 5

| | Example | | | |
|---|---|---|---|---|
| | 17 | 18 | 19 | 20 |
| COMPOSITION (wt %) | | | | |
| CaO | 5.9 | 4.9 | 4.3 | 6.0 |
| $K_2O$ | 2.1 | 1.8 | 0.6 | 1.5 |
| $Na_2O$ | 0.5 | — | 0.2 | — |
| MgO | 26.1 | 20.0 | 34.6 | 21.5 |
| $SiO_2$ | 43.4 | 47.4 | 33.0 | 43.2 |
| $Al_2O_3$ | 11.4 | 12.5 | 10.0 | 13.1 |
| $ZrO_2$ | 2.5 | 8.2 | 9.5 | 6.2 |
| F | 8.1 | 5.2 | 7.8 | 5.5 |
| SrO | | | | 1.5 |
| $TiO_2$ | | | | 0.5 |
| $Y_2O_3$ | | | | 1.0 |
| Temperature for heat treatment (°C) | 950 | 950 | 950 | 950 |
| Time for heat treatment (h) | 2 | 2 | 2 | 2 |
| Precipitated crystals | mica zirconia enstatite | mica zirconia enstatite | mica zirconia diopside | mica zirconia |
| Bending strength (MPa) | 350 | 320 | 310 | 400 |
| Machinability | B | A | B | B |

Machinability:
A : excellently machinable
B : well machinable
C : machinable

TABLE 6

| | Example | | |
|---|---|---|---|
| | 21 | CEx-1 | CEx-2 |
| COMPOSITION (wt %) | | | |
| CaO | 5.3 | 8.0 | 4.4 |
| $K_2O$ | 2.5 | — | 1.8 |
| $Na_2O$ | 0.9 | — | — |
| MgO | 24.5 | 28.0 | 23.6 |
| $SiO_2$ | 39.5 | 41.8 | 35.2 |
| $Al_2O_3$ | 12.1 | 11.4 | 9.9 |
| $ZrO_2$ | 5.3 | 2.0 | 17.7 |
| F | 7.9 | 8.8 | 7.4 |
| $Nb_2O_5$ | 0.5 | | |
| $Ta_2O_5$ | 1.5 | | |
| Temperature for heat treatment (°C) | 950 | 850 | — |
| Time for heat treatment (h) | 2 | 10 | — |
| Precipitated crystals | mica zirconia diopside | mica zirconia | nil |
| Bending strength (MPa) | 335 | — | — |
| Machinability | B | — | — |

Machinability:
A : excellently machinable
B : well machinable
C : machinable
CEx = Comparative Example As is clearly shown in Tables 1 to 6, the glass-ceramics obtained in Examples 1 to 21 had a high bending strength of 250 to 550 MPa or were excellent in mechanical strength, and these glass-ceramics were also excellent in machinability.

Further, the above glass-ceramics were tested on chemical durability as follows; Samples prepared from the above glass-ceramics were individually immersed in 90 ml of a 10% HCl aqueous solution at room temperature for 24 hours, and other samples prepared from the above glass-ceramics were individually immersed in 90 ml of a 10% NaOH aqueous solution under the same conditions. Then, each of these samples was measured for a weight loss, and the results were taken as acid durability data and alkali durability data. The glass-ceramics obtained in Examples 1 to 21 showed a weight loss of not more than 0.50 mg/cm² in the acid durability test and a weight loss of not more than 0.04 mg/cm² in the alkali durability test. That is, these glass-ceramics showed excellent chemical durability.

COMPARATIVE EXAMPLE 1

Example 1 was repeated except that the raw materials were used in such amounts that a glass-ceramic having the composition shown in Table 1 was obtained. The thus-obtained glass-ceramic showed swelling properties, and was disintegrated after 3 days.

COMPARATIVE EXAMPLE 2

The raw materials were mixed and the mixture was melted at 1,550° C. so that a glass-ceramic having the composition shown in Table 1 was obtained. This mixture did not give any homogeneous melt, and no glass could be obtained.

EXAMPLES 22–28

Glass Ceramics

Oxides, carbonates, fluorides, etc., such as $CaCO_3$, $K_2CO_3$, $Na_2CO_3$, MgO, $MgF_2$, $Al_2O_3$, $SiO_2$ and $ZrO_2$ were used as raw materials. These raw materials were mixed in such proportions that glass-ceramics having compositions shown in Tables 7 and 8 were obtained. The resultant mixtures were respectively charged into a platinum crucible and melted at 1,400° to 1,550° C. for 60 to 120 minutes. Then, each melted glass was cast, and annealed to room temperature to give a bulk glass. These bulk glasses had a glass transition point between 550° C. and 650° C. The bulk glasses were placed in an electric furnace, heated from room temperature to a predetermined temperature in the range of 550° to 800° C. (corresponding to a temperature higher than the glass transition point by 10° to 200° C.) at a constant temperature elevation rate of 3° C./minute, and kept at the predetermined temperature for 2 to 100 hours. Thereafter, the bulk glasses were heated up to a predetermined temperature in the range of 800° to 1,200° C. (corresponding to a temperature higher than the glass transition point by 200° to 500° C.) at a constant temperature elevation rate of 3° C./minute, and crystallized at the predetermined temperature for 2 to 10 hours. Then, the resultant products were cooled to room temperature in the furnace to give glass-ceramics of Examples 22 to 28. Part of each of the above-obtained glass-ceramics was pulverized, and precipitated crystals were identified by X-ray diffraction. Further, these glass-ceramics were measured for bending strength and cutting processability in the same manner as in Examples 1 to 21. Tables 7 and 8 show the results.

TABLE 7

| | Example | | | |
|---|---|---|---|---|
| | 22 | 23 | 24 | 25 |
| COMPOSITION (wt %) | | | | |
| CaO | 4.9 | 4.6 | 6.3 | 3.9 |
| $K_2O$ | 1.9 | 1.7 | 2.1 | 1.6 |
| $Na_2O$ | 0.8 | — | 1.7 | 1.4 |
| MgO | 19.6 | 18.9 | 24.5 | 32.1 |
| $SiO_2$ | 42.6 | 44.7 | 43.4 | 37.6 |
| $Al_2O_3$ | 16.0 | 18.6 | 11.4 | 9.2 |
| $ZrO_2$ | 5.8 | 6.6 | 3.0 | 8.2 |
| F | 8.4 | 4.9 | 7.6 | 6.0 |
| Temperature for heat treatment (°C.) | 650 | 650 | 700 | 720 |
| Time for heat treatment (h) | 10 | 5 | 5 | 10 |
| Temperature for heat treatment (°C.) | 950 | 970 | 950 | 980 |
| Time for heat treatment (h) | 2 | 2 | 2 | 2 |
| Precipitated crystals | mica zirconia enstatite | mica zirconia enstatite | mica zirconia | mica zirconia diopside |
| Bending strength (MPa) | 310 | 270 | 350 | 380 |

TABLE 7-continued

| | Example | | | |
|---|---|---|---|---|
| | 22 | 23 | 24 | 25 |
| Machinability | B | B | B | A |

Machinability:
A : excellently machinable
B : well machinable
C : machinable

TABLE 8

| | Example | | |
|---|---|---|---|
| | 26 | 27 | 28 |
| COMPOSITION (wt %) | | | |
| CaO | 6.0 | 2.5 | 7.5 |
| $K_2O$ | 1.6 | 0.4 | 1.5 |
| $Na_2O$ | 1.9 | 0.2 | 0.3 |
| MgO | 21.8 | 15.1 | 23.8 |
| $SiO_2$ | 40.3 | 47.9 | 41.5 |
| $Al_2O_3$ | 11.8 | 19.5 | 11.4 |
| $ZrO_2$ | 7.2 | 4.5 | 6.2 |
| F | 9.4 | 9.9 | 7.8 |
| Temperature for heat treatment (°C.) | 670 | 600 | 650 |
| Time for heat treatment (h) | 20 | 100 | 30 |
| Temperature for heat treatment (°C.) | 940 | 950 | 900 |
| Time for heat treatment (h) | 2 | 2 | 2 |
| Precipitated crystals | mica zirconia diopside | mica zirconia enstatite diopside | mica zirconia enstatite diopside |
| Bending strength (MPa) | 400 | 380 | 430 |
| Machinability | B | B | C |

Machinability:
A : excellently machinable
B : well machinable
C : machinable

As is clearly shown in Tables 7 and 8, the glass-ceramics obtained in Examples 22 to 28 had a high bending strength of 270 to 430 MPa, and were also excellent in machinability. Further, the controlling of the composition and the heat treatment temperature for each glass-ceramic made it possible to precipitate a fine crystal having a size of 1 μm or less, and glass-ceramics having light transmission property could be obtained.

The above-obtained glass-ceramics were also measured for chemical durability values in the same manner as in Examples 1 to 21 to show that the glass-ceramics showed a weight loss of not more than 0.50 mg/cm² in the acid durability test and a weight loss of not more than 0.04 mg/cm² in the alkali durability test.

EXAMPLE 29

Artificial Dental Crown

A mixture of raw materials, which were to give a glass-ceramic having the composition shown in Example 11, was melted at 1,500° C. for 90 minutes. Then, the melted glass was cast into a mold formed from a dental non-gypsum refractory investment material and annealed to room temperature to give a glass having the form of a dental crown.

The above-obtained glass was placed in an electric furnace, heated from room temperature up to 950° C. at a rate of 3° C./min, crystallized at this temperature for 2 hours, and cooled to room temperature to give a dental crown formed of the glass-ceramic having the predetermined form.

EXAMPLE 30

Artificial Dental Crown

A mixture of raw materials, which were to give a glass-ceramic having the composition shown in Example 26, was melted and cast in the same manner as in Example 29 to give a glass having the form of a dental crown.

The above-obtained glass was placed in an electric furnace, heated from room temperature up to 670° C. at a rate of 3° C./min, kept at this temperature for 2 hours, then heated up to 940° C. at a rate of 3° C./min, and crystallized at this temperature for 2 hours. Thereafter, the product was cooled to room temperature to give a dental crown formed of the glass-ceramic having the predetermined form.

EXAMPLE 31

Artificial Dental Crown

A block having a size of 20×20×50 mm was taken from the glass-ceramic obtained in Example 3, and processed with a lathe, a drilling machine and dental tools to give a dental crown formed of the glass-ceramic having a predetermined form.

EXAMPLE 32

Artificial Dental Crown

The glass-ceramic having light transmission property, obtained in Example 25, was treated in the same manner as in Example 31 to give a dental crown formed of the glass-ceramic having light transmission property.

The glass-ceramics of Examples 5, 8, 9, 13, 16 and 23 out of the above glass-ceramics were analyzed for actual contents of their components. Table 9 shows the results.

The contents of the oxides and fluorine in the glass-ceramics of Examples 5, 8, 9, 13, 16 and 23 were analyzed as follows.

(1) CaO, MgO, $SiO_2$, $Al_2O_3$ and $ZrO_2$

Analyzed with an ICP emission spectrophotometer SPS1200VR supplied by Seiko Denshi Kogyo.

The measurement conditions for the ICP emission spectrochemical analysis were as follows.

Measurement wavelength: Zr (339.198 nm), Si (251.611 nm), Al (396.152 nm), Ca (317.933 nm), Mg (285.213 nm).
RF power: 1.3 [kV]
Photometric height: 12.0 [mm]
Integral time: 3.0 [sec]
Number of integration: 3 [times]

(2) $K_2O$ and $Na_2O$

Analyzed with an atomic absorption spectrochemical analyzer SAS760 supplied by Seiko Denshi Kogyo.

The measurement conditions for the flame analysis were as follows.

Measurement wavelength: K (766.5 nm), Na (589.0 nm)
Photometric mode: INTEG
Lamp electric current: 10 [mA]
Integral time: 5 [sec]
Response time: 1.00 [sec]
Slit width: 0.54 [mm]
Burner height: K: 8 [mm], Na: 10 [mm]
Burner angle: 0 [°]
Combustion gas: acetylene (3.5 [l/min])
Supporting gas: air (17 [l/min])

(3) Fluorine (i) Preparation of a powder sample

A ceramic containing fluorine was pulverized, and 0.1 to 0.15 g of the resultant powder was put in a platinum boat and measured for its weight. Then, about 0.7 g of an $\alpha$-$Al_2O_3$ powder as a reaction promoter was added to, and mixed with, the powder in the platinum boat to prepare a powder sample for the determination of the fluorine content.

(ii) Apparatus for the determination of fluorine content

The apparatus shown in FIG. 1 was used. In FIG. 1, a steam-generating flask 1 contains distilled water 2, and steam is generated by heating it with a burner 3. The steam-generating flask 1 communicates with a silica reaction tube 5 through a pipe $P_1$.

The silica reaction tube 5 is provided with an electric tubular furnace 6 around its central portion, and the

TABLE 9

| | Example | | | | | | | | | | | |
|---|---|---|---|---|---|---|---|---|---|---|---|---|
| | 5 | | 8 | | 9 | | 13 | | 16 | | 23 | |
| | Found | Predetermined*1 | Found | Predetermined*1 | Found | Predetermined*2 | Found | Predetermined*3 | Found | Predetermined*3 | Found | Predetermined*4 |
| COMPOSITIONS (wt %) | | | | | | | | | | | | |
| CaO | 5.4 | 5.4 | 8.8 | 8.9 | 8.3 | 8.1 | 3.2 | 3.2 | 5.3 | 5.2 | 4.6 | 4.6 |
| $K_2O$ | 2.5 | 2.2 | 4.0 | 3.7 | 1.3 | 0.8 | 0.7 | 0.5 | 2.2 | 2.0 | 2.2 | 1.7 |
| $Na_2O$ | 1.0 | 0.8 | 4.0 | 3.9 | 4.0 | 3.7 | 0.3 | 0.2 | 1.0 | 0.9 | 0.1 | 0 |
| MgO | 23.6 | 21.9 | 16.7 | 16.0 | 20.3 | 20.4 | 26.3 | 25.0 | 22.0 | 20.8 | 19.7 | 18.9 |
| $SiO_2$ | 40.2 | 40.3 | 44.6 | 45.1 | 35.8 | 33.5 | 39.5 | 39.2 | 44.8 | 45.2 | 44.4 | 44.7 |
| $Al_2O_3$ | 12.2 | 11.7 | 9.2 | 8.7 | 25.8 | 29.1 | 17.8 | 17.4 | 13.8 | 13.0 | 19.0 | 18.6 |
| $ZrO_2$ | 8.9 | 10.6 | 6.8 | 7.3 | 2.9 | 2.8 | 2.5 | 2.5 | 3.9 | 4.0 | 6.1 | 6.6 |
| F | 6.2 | 7.1 | 5.9 | 6.4 | 1.5 | 1.6 | 9.6 | 12.0 | 7.0 | 8.9 | 4.1 | 4.9 |

*1 from Table 2
*2 from Table 3
*3 from Table 4
*4 from Table 7

It has been found that, as shown in Table 9, the found values of the oxides constituting the glass-ceramics of Examples 5, 8, 9, 13, 16 and 23 were nearly in agreement with predetermined values of the oxides of the corresponding glass-ceramics, and that the found values of fluorine were generally lower than the predetermined values. The reason for this discrepancy concerning the fluorine is presumably that part of fluorine dissipates during the preparation of the glass from the mixture of raw materials and during the formation of the glass-ceramic.

silica reaction tube 5 is heated with it thereby to heat a platinum boat 7 containing a powder sample. The temperature of the silica reaction tube 5 is measured with a thermocouple 8.

Further, the silica reaction tube communicates with a condenser 9, and steam which has contacted the powder sample is condensed with the condenser 9. A pipe $P_2$ connected to the condenser 9 has a length sufficient to reach a sodium hydroxide aqueous solution 11 in a flask 10, and water formed by condensation flows down the pipe $P_2$.

The sodium hydroxide aqueous solution 11 in the flask 10 is a mixture of 2 to 3 ml of 1N-NaOH (concentration known) with 100 ml of distilled water.

(3) Method of determination of the fluorine content

The fluorine content was determined by the following procedures (i) to (iv).

(i) The silica reaction tube 5 was temperature-elevated up to 1,200° C. with the electric tubular furnace 6. This temperature was measured with the thermocouple 8. Then, the distilled water 2 in the steam-generating flask 1 was heated and boiled with the burner 3 to supply the silica reaction tube 5 with steam through the pipe $P_1$ while adjusting the burner 3 so that the amount of water formed by condensation in the condenser 9 was 3 to 4 ml/minute, and this state was kept for about 10 minutes.

(ii) A purge cock 4 was opened to stop the supply of steam to the pipe $P_1$, the temperature of the electric tubular furnace 6 was decreased to 1,000° C., and the platinum boat 7 containing a powder sample was placed in the silica reaction tube 5.

(iii) The purge cock 4 was closed to re-supply the silica reaction tube 5 with steam through the pipe $P_1$, and the silica reaction tube 5 was temperature-increased to 1,200° C. to allow fluorine in the sample to react with steam for about 30 minutes.

(iv) After the reaction, the steam was condensed with the condenser 9, and water formed by condensation was introduced into the flask 10 through the pipe $P_2$ to allow the sodium hydroxide aqueous solution 11 to absorb it. One or two drops of phenolphthalein as an indicator was added to the sodium hydroxide aqueous solution 11 in the flask 10, and a point of neutralization was determined by titration with 0.1N-HCl (concentration known), whereby the amount of collected fluorine was determined and the fluorine content in the glass was determined.

After the measurements (1), (2) and (3), the contents of components (various oxides and fluorine) were calculated, the total contents of various oxides and fluorine being 100% by weight. The results are shown in Table 9.

As specified above, the glass-ceramic containing CaO, $K_2O$, $Na_2O$, MgO, $SiO_2$, $Al_2O_3$ and fluorine in the specific amount ranges and having at least a precipitated zirconia crystal and a precipitated mica crystal is advantageously excellent in mechanical strength, machinability (cutting processability) and chemical durability. And, an excellent artificial dental crown can be obtained from this glass-ceramic.

What is claimed is:

1. A glass-ceramic containing, by weight percentage,

| | |
|---|---|
| CaO | 2-17%, |
| $K_2O$ | 0-5% |
| $Na_2O$ | 0-4% | the total content of $K_2O$ and $Na_2O$ being 0.5-7%,

| | |
|---|---|
| MgO | 15-35% |
| $SiO_2$ | 30-49% |
| $Al_2O_3$ | 5-30% |
| $ZrO_2$ | 2-15%, and |
| fluorine (calculated as F) | not more than 14%, | and having at least a zirconia crystal and a mica crystal precipitated.

2. A glass-ceramic according to claim 1, wherein the fluorine is contained in an amount of 1.5 to 14% by weight.

3. A glass-ceramic according to claim 1, wherein the CaO is contained in an amount of 5 to 15% by weight, the $K_2O$ is contained in an amount of 1 to 3.5% by weight, the $Na_2O$ is contained in an amount of 0.5 to 1.8% by weight, the total amount of the $K_2O$ and the $Na_2O$ is 1.5 to 5.3% by weight, MgO is contained in an amount of 19 to 30% by weight, the $SiO_2$ is contained in an amount of 40 to 49% by weight, the $Al_2O_3$ is contained in an amount of 7 to 17% by weight, the $ZrO_2$ is contained in an amount of 3 to 12% by weight, and the fluorine is contained in an amount of 7 to 14% by weight.

4. A glass-ceramic according to claim 1, which further contains not more than 5% by weight of at least one oxide selected from SrO, $TiO_2$, $Nb_2O_5$, $Ta_2O_5$ and $Y_2O_3$.

5. A glass-ceramic according to claim 1, which further has at least one precipitated crystal selected from an enstatite crystal, an akermanite crystal, a diopside crystal, an anorthite crystal, a richterite crystal and a forsterite crystal.

6. An artificial dental crown, which is formed from the glass-ceramic recited in claim 1.

* * * * *